United States Patent [19]

Nappa et al.

[11] Patent Number: 5,274,190
[45] Date of Patent: Dec. 28, 1993

[54] PROCESS FOR THE MANUFACTURE OF LINEAR HYDROFLUOROCARBONS CONTAINING END GROUP HYDROGEN SUBSTITUENTS

[75] Inventors: Mario J. Nappa, Newark, Del.; Allen C. Sievert, Elkton, Md.

[73] Assignee: E. I. Du Pont de Nemours and Company, Wilmington, Del.

[21] Appl. No.: 66,448

[22] Filed: May 24, 1993

[51] Int. Cl.$^5$ .............................................. C07C 21/18
[52] U.S. Cl. .................................................. 570/142
[58] Field of Search ....................................... 570/142

[56] References Cited

U.S. PATENT DOCUMENTS

| | | | |
|---|---|---|---|
| 2,666,797 | 5/1950 | Husted et al. | 260/633 |
| 2,993,925 | 7/1961 | Husted | 260/448.8 |
| 3,742,010 | 6/1973 | Hardies et al. | |
| 4,346,250 | 8/1982 | Satokawa et al. | 568/842 |
| 4,745,235 | 5/1988 | Ashton | 570/142 |
| 4,766,260 | 8/1988 | Manzer et al. | 570/168 |
| 4,902,838 | 2/1990 | Manzer et al. | 570/151 |

FOREIGN PATENT DOCUMENTS

| | | |
|---|---|---|
| 65857/90 | 5/1991 | Australia. |
| WO93/02150 | 2/1993 | PCT Int'l Appl. . |
| 0635083 | 12/1978 | U.S.S.R. ............. 570/142 |

OTHER PUBLICATIONS

W. V. Cohen, *J. Org. Chem.* 26:4021–4026 (1961).
No, et al., *Zhur. Org. Khim.* 12(8):1825 (Aug. 1976).
Ashton, et al., *J. Flourine Chem.* 27:263–274 (1985).
Christie, et al., *Aromatic Flourine Compounds* IV, pp. 559–560 (Feb. 1966).
*Chemical Abstracts*, 85:159314g.

*Primary Examiner*—Alan Siegel

[57] ABSTRACT

Linear hydrofluorocarbons of the formula $XCF_2(CF_2)_nCH_2F$ where X is H or F, and n is 1 to 7 when X is H and 0 to 7 when X is F, are produced by a vapor phase catalytic reaction of HF with corresponding compounds of the formula $XCF_2(CF_2)_nCH_2OY$ where Y is $-(CO)Cl$ or $-SO_2Cl$.

10 Claims, No Drawings

PROCESS FOR THE MANUFACTURE OF LINEAR HYDROFLUOROCARBONS CONTAINING END GROUP HYDROGEN SUBSTITUENTS

FIELD OF THE INVENTION

This invention relates to a process for producing fluorine-substituted aliphatic hydrocarbons, and more particularly to a process for producing linear hydrofluorocarbons containing end group hydrogen substituents.

BACKGROUND

There has been recent concern that completely halogenated chlorofluorocarbons might be detrimental toward the Earth's ozone layer. Consequently, there is a world-wide effort to use halogen-substituted hydrocarbons which contain fewer chlorine substituents. For example, 1,1,1,2-tetrafluoroethane (HFC-134a), a hydrofluorocarbon having zero ozone depletion potential, is being considered as a replacement for dichlorodifluoromethane (CFC-12) in refrigeration systems. The production of hydrofluorocarbons (i.e., compounds containing only carbon, hydrogen and fluorine) has been the subject of renewed interest to provide environmentally desirable products for use as solvents, blowing agents, refrigerants, cleaning agents, aerosol propellants, heat transfer media, dielectrics, fire extinguishants and power cycle working fluids (see, e.g., PCT International Publication No. WO93/02150).

SUMMARY OF THE INVENTION

A process is provided in accordance with this invention for producing a linear hydrofluorocarbon of the formula $XCF_2(CF_2)_nCH_2F$, where X is H or F, and where n is an integer from 1 to 7 when X is H and n is an integer from 0 to 7 when X is F. The process comprises the step of feeding a compound of the formula $XCF_2(CF_2)_nCH_2OY$, where X and n are as defined above and Y is $-(CO)Cl$ or $-SO_2Cl$ and hydrogen fluoride to a reactor containing a catalyst selected from the group consisting of aluminum fluoride, fluorided alumina, metal supported on aluminum fluoride, metal supported on fluorided alumina, and mixtures thereof; and reacting said compound with said hydrogen fluoride in said reactor in the vapor phase over said catalyst at an elevated temperature.

DETAILED DESCRIPTION

This invention provides a process for producing hydrofluorocarbons of the formula, $CF_3(CF_2)_nCH_2F$, where n is an integer from 0 to 7 and of the formula, $HCF_2(CF_2)_nCH_2F$, where n is an integer from 1 to 7. These hydrofluorocarbons are prepared from corresponding chloroformate and/or chlorosulfate esters. Chloroformates of the formula $XCF_2(CF_2)_nCH_2(CO)Cl$ (i.e., Y equals $-(CO)Cl$) can be advantageously prepared by known art methods such as the reaction of the corresponding alcohol, $XCF_2(CF_2)_nCH_2OH$, with phosgene ($COCl_2$) in the presence of base and isolating the chloroformate ester. Chlorosulfates of the formula $XCF_2(CF_2)_nCH_2OSO_2Cl$ (i.e., Y equals $-SO_2Cl$) can be advantageously prepared by known art methods such as the reaction of the corresponding alcohol, $XCF_2(CF_2)_nCH_2OH$, with sulfuryl chloride ($SO_2Cl_2$) in the presence of base, and isolating the chlorosulfate ester. Alcohols of the structure, $CF_3(CF_2)_nCH_2OH$, where n is an integer from 0 to 7, can be prepared by known methods using lithium aluminum hydride to reduce the corresponding acids. Alcohols of the structure, $HCF_2(CF_2)_nCH_2OH$, where n is an integer from 1 to 7, can be prepared by known methods by the reaction of methanol and tetrafluoroethylene as described in U.S. Pat. No. 4,346,250 and in Chem. Abst. 85:159314g. Of particular interest is the preparation of 2,2,3,3-tetrafluoropropanol (TFP), the alcohol where X is H and n is 1, and corresponding esters thereof. TFP can be prepared by reacting methanol with tetrafluoroethylene as described in U.S. Pat. No. 4,346,250. Phosgene may be reacted with TFP to produce $CHF_2CF_2CH_2O(CO)Cl$ as described in U.S. Pat. No. 3,742,010. Sulfuryl chloride may be reacted with TFP to produce $CHF_2CF_2CH_2OSO_2Cl$ as described in W. V. Cohen, J. Org. Chem., 26, 4021–4026 (1961).

The chloroformate or chlorosulfate esters of $XCF_2(CF_2)_nCH_2OH$ are reacted with hydrogen fluoride over a catalyst comprising aluminum fluoride and/or fluorided alumina. Catalysts which may be used in accordance with this invention include fluorided alumina, aluminum fluoride, metals on aluminum fluoride, and metals on fluorided alumina. Fluorided alumina and aluminum fluoride can be prepared as described in U.S. Pat. No. 4,902,838. Suitable metals include chromium, magnesium (e.g., magnesium fluoride), Group VIIB metals (e.g., manganese), Group IIIB metals (e.g., lanthanum), and zinc. In use, such metals are normally present as halides (e.g., fluorides), as oxides, and/or as oxyhalides. Preferably, when supported metals are used, the total metal content of the catalyst if from about 0.1 to 20 percent by weight, typically from about 0.1 to 10 percent by weight. Metals on aluminum fluoride and metals on fluorided alumina can be prepared by procedures described in U.S. Pat. No. 4,766,260. Preferred catalysts include catalysts consisting essentially of aluminum fluoride and/or fluorided alumina.

Normally the molar ratio of HF to compounds of the formula $XCF_2(CF_2)_nCH_2O(CO)Cl$ or $XCF_2(CF_2)_nCH_2OSO_2Cl$ ranges from about 100:1 to about 0.5:1, and is preferably from about 50:1 to 0.75:1, and more preferably from about 10:1 to 1:1. Typically, the amount of HF is at least a stoichiometric amount.

The reaction of $XCF_2(CF_2)_nCH_2O(CO)Cl$ or $XCF_2(CF_2)_nCH_2OSO_2Cl$ with HF in the presence of the catalysts of the instant invention is Suitably conducted in the vapor phase at a temperature in the range of from about 200° C. to about 450° C., preferably from about 225° C. to about 350° C., and more preferably from about 250° C. to about 300° C. The contact time is typically from about 1 to about 120 seconds, and is preferably from about 10 to 40 seconds.

Pressure is not critical. Atmospheric and superatmospheric pressures (e.g., pressures from about 100 kPa to 7000 kPa) are the most convenient and are therefore preferred.

The reaction products may be separated by conventional techniques, such as distillation. Hydrofluorocarbons of the formula $XCF_2(CF_2)_nCH_2F$ likely form azeotropes with HF; and conventional decantation/distillation may be employed if further purification of the hydrofluorocarbons is desired.

The reaction of $XCF_2(CF_2)_nCH_2O(CO)Cl$ or $XCF_2(CF_2)_nCH_2OSO_2Cl$ with HF may be conducted in any suitable reactor, including fixed and fluidized bed reactors. The reaction vessel should be constructed from materials which are resistant to the corrosive effects of hydrogen fluoride such as Inconel ™ nickel alloy and Hastelloy ™ nickel alloy.

Hydrofluorocarbons of the formula $XCF_2(CF_2)_nCH_2F$ have numerous uses including applications in compositions used as refrigerants, blowing agents, propellants, cleaning agents, and heat transfer agents.

Practice of the invention will become further apparent from the following non-limiting examples.

EXAMPLE 1

$CHF_2CF_2CH_2O(CO)Cl \rightarrow CHF_2CF_2CH_2F$

A 15 in (38.1 cm) x 3/8 in (0.95 cm) Hastelloy ® nickel alloy tube was filled with 8.07 g (about 13 mL) of gamma-alumina ground to 12/20 mesh (1.68/0.84 mm).

A. Catalyst Activation

The catalyst was activated by heating at 175° C. for 35 minutes under a nitrogen purge (25 sccm, $4.2 \times 10^{-7}$ m³/s). HF was fed at 25 sccm ($4.2 \times 10^{-7}$ m³/s) for 63 minutes and a temperature rise to 179° C. was noted. The temperature was raised to 250° C., the HF flow increased to 40 sccm ($6.7 \times 10^{-7}$ m³/s), and the $N_2$ flow decreased to 10 sccm ($1.7 \times 10^{-7}$ m³/s) for 43 minutes. An exotherm to 255° C. was noted. The temperature was raised to 350° C. while maintaining flows for 30 minutes, and then the temperature was raised to 400° C. while maintaining flows for 144 minutes. The flow of HF was reduced to 5 sccm ($8.3 \times 10^{-8}$ m³/s) and the $N_2$ flow to 5 sccm ($8.3 \times 10^{-8}$ m³/s) for 15.3 hours (overnight).

B. Reaction

The reactor was cooled to 250° C. The $CHF_2CF_2CH_2O(CO)Cl$ flow of 0.35 mL/hr (1.12 sccm, $1.87 \times 10^{-8}$ m³/s), the HF flow of 10.6 sccm ($1.8 \times 10^{-7}$ m³/s), and a $N_2$ flow of 2 sccm ($3.3 \times 10^{-8}$ m³/s) were begun. The gaseous effluent was analyzed by gas chromatography/mass spectroscopy (i.e., GCMS) and found to be 96.6–98.7% $CHF_2CF_2CH_2F$ over a 24 hour period.

EXAMPLE 2

$CHF_2CF_2CH_2O(CO)Cl \rightarrow CHF_2CF_2CH_2F$

A 15 in (38.1 cm) × ⅜ in (0.95 cm) Hastelloy ® nickel alloy tube was filled with 9.10 g (about 13 mL) of $AlF_3 \cdot 3H_2O$ ground to 12/20 mesh (1.68/0.84 mm).

A. Catalyst Activation

The catalyst was activated by heating at 400° C. for 65 minutes under a nitrogen purge (50 sccm, $8.3 \times 10^{-7}$ m³/s). The $N_2$ flow was reduced to 2 sccm ($3.3 \times 10^{-8}$ m³/s), and HF was fed at 10 sccm ($1.7 \times 10^{-7}$ m³/s) for 75 minutes and a temperature rise to 409° C. was noted. The temperature was lowered to 250° C., the HF flow increased to 20 sccm ($3.3 \times 10^{-7}$ m³/s) while maintaining the same $N_2$ flow for 20 minutes. An exotherm to 253° C. was noted.

B. Reaction

The $CHF_2CF_2CH_2O(CO)Cl$ flow of 0.35 mL/hr (1.12 sccm, $1.87 \times 10^{-8}$ m³/s), the HF flow of 10.6 sccm ($1.8 \times 10^{-7}$ m³/s), and a $N_2$ flow of 2 sccm ($3.3 \times 10^{-8}$ m³/s) were begun. The gaseous effluent was analyzed by GCMS and found to be 95–96.3% $CHF_2CF_2CH_2F$ over a 4 hour period. The flow of HF was reduced to 10.9 sccm ($1.8 \times 10^{-7}$ m³/s) and the gaseous effluent was analyzed by GCMS and found to be 98.0–98.3% $CHF_2CF_2CH_2F$ over a 3 hour period.

EXAMPLE 3

$CHF_2CF_2CH_2F$

The catalyst used was prepared as described in Example 1 and cooled to 275° C.

Reaction

The $CHF_2CF_2CH_2OSO_2Cl$ flow of 0.68 mL/hr (2.0 sccm, $3.3 \times 10^{-8}$ m³/s), the HF flow of 15.0 sccm ($2.5 \times 10^{-7}$ m³/s), and a $N_2$ flow of 2 sccm ($3.3 \times 10^{-8}$ m³/s) were begun. The gaseous effluent was analyzed by GCMS and found to have 65% conversion of $CHF_2CF_2CH_2OSO_2Cl$ with a selectivity of 65% for $CHF_2CF_2CH_2F$ (HFC-245ca) and 28% for $CHF_2CF_2CH_2OSO_2F$. $CHF_2CF_2CH_2OSO_2F$ can be recycled back to the fluorination reactor to afford additional HFC-245ca.

COMPARATIVE EXAMPLE A $CCl_3CH_2O(CO)Cl \rightarrow CHCl=CCl_2$

The catalyst (8.10 gm) was prepared and used in the reactor described in Example 1. The temperature of the catalyst was lowered to 225° C. The $CCl_3CH_2O(CO)Cl$ flow of 0.79 mL/hr (2.24 sccm, $3.73 \times 10^{-8}$ m³/s), the HF flow of 10.8 sccm ($1.8 \times 10^{-7}$ m³/s), and a $N_2$ flow of 2 sccm ($3.3 \times 10^{-8}$ m³/s) were begun. The gaseous effluent was analyzed by GCMS and found to be 88–92% trichloroethylene over a 2 hour period. No $CH_2ClCF_3$ or $CH_2FCF_3$ was identified.

Particular embodiments of the invention are illustrated by the examples. Other embodiments will become apparent to those skilled in the art from a consideration of the specification or practice of the invention disclosed herein. It is understood that modifications and variations may be practiced without departing from the spirit and scope of the novel concepts of this invention. It is further understood that the invention is not confined to the particular formulations and examples herein illustrated, but it embraces such modified forms thereof as come within the scope of the following claims.

What is claimed is:

1. A process for producing a linear hydrofluorocarbon of the formula $XCF_2(CF_2)_nCH_2F$ wherein X is selected from the group consisting of H and F and wherein n is an integer from 0 to 7 when X is F and an integer from 1 to 7 when X is H, comprising the steps of:

feeding a compound of the formula $XCF_2(CF_2)_nCH_2OY$ wherein X and n are as defined above and Y is selected from the group consisting of —(CO)Cl and —SO₂Cl and hydrogen fluoride to a reactor containing a catalyst selected from the group consisting of aluminum fluoride, fluorided alumina, metal supported on aluminum fluoride, metal supported on fluorided alumina, and mixtures thereof; and reacting said compound with said hydrogen fluoride in said reactor in the vapor phase over said catalyst at an elevated temperature.

2. The process of claim 1 wherein Y is —(CO)Cl.

3. The process of claim 2 further comprising the step of preparing said compound of the formula $XCF_2(CF_2)_nCH_2(CO)Cl$ by reacting an alcohol of the formula $XCF_2(CF_2)_nCH_2OH$ with phosgene.

4. The process of claim 3 wherein n is 1, wherein 2,2,3,3-tetrafluoropropanol is produced by reacting methanol with tetrafluoroethylene, and wherein phosgene is reacted with said 2,2,3,3-tetrafluoropropanol.

5. The process of claim 1 wherein Y is —$SO_2Cl$.

6. The process of claim 5 further comprising the step of preparing said compound of the formula $XCF_2(CF_2)_nCH_2SO_2Cl$ by reacting an alcohol of the formula $XCF_2(CF_2)_nCH_2OH$ with surfuryl chloride.

7. The process of claim 5 wherein 2,2,3,3-tetrafluoropropanol is produced by reacting methanol with tetrafluoroethylene, and wherein surfuryl chloride is reacting with said 2,2,3,3-tetrafluoropropanol.

8. The process of claim 1 wherein the catalyst consists essentially of aluminum fluoride and/or fluorided alumina.

9. The process of claim 1 wherein the reaction with HF is at a temperature within the range of 200° C. to 400° C.

10. The process of claim 1 wherein the mole ratio of HF to compounds of the formula $XCF_2(CF_2)_nCH_2OY$ fed to the reactor is from about 100:1 to 1:1.

* * * * *